United States Patent [19]
Romanowski et al.

[11] Patent Number: 5,847,157
[45] Date of Patent: Dec. 8, 1998

[54] METHOD OF PRODUCING (+) 2-AZABICYCLO{2.2.1}HEPT-5-EN-3-ONE

[75] Inventors: Frank Romanowski, Borgerhout; Kurt Vroman, Morkhoven; Rudolf Vanheertum, Antwerp, all of Belgium

[73] Assignee: Degussa Aktiengesellschaft, Frankfurt, Germany

[21] Appl. No.: 882,292

[22] Filed: Jun. 25, 1997

[30] Foreign Application Priority Data

Jun. 25, 1996 [DE] Germany .................. 196 25 323.3

[51] Int. Cl.$^6$ ................................. C07D 209/52
[52] U.S. Cl. ............................................. 548/512
[58] Field of Search ............................ 548/512; 546/112

[56] References Cited

U.S. PATENT DOCUMENTS 5,300,649   4/1994   Griffiths et al. .................. 546/290

FOREIGN PATENT DOCUMENTS 0 508 352   10/1992   European Pat. Off. .
0 533 048   3/1993   European Pat. Off. .

OTHER PUBLICATIONS

Katagiri et al., Hetero Diels–Alder Reaction of Benzenesulfonyl Cyanide with Cyclopentadiene Using Chiral Lewis Acids, Chem. Pharm. Bull. vol. 44, No. 4, (1996) pp. 850–852.

Griffiths et al., Diels–Alder Reaction of Methanesulfonyl Cyanide with Cyclopentadiene. Industrial Synthesis of 2–Azabicyclo[2.2.1]hept–5–en–3–one, J. Org. Chem. vol. 58, No. 22 (1993) pp. 6129–6131.

Daluge et al., Synthesis of Carbocyclic Aminonucleosides, J. Org. Chem. vol. 43, No. 12 (1978) pp. 2311–2320.

Jagt et al., Diels–Alder Cycloadditions of Sulfonyl Cyanides with Cyclopentadiene. Synthesis of 2–Azabicyclo[2.2.1] hepta–2,5–dienes, J. Org. Chem. vol. 39, No. 4 (1974) pp. 564–566.

Shirakawa et al., Preparation of 2–azabicyclo[2.2.1]hept–5–en–3–one by Cyclocondensation of Cyclopentadiene with Phenylsulfonyl Cyanide, Chemical Abstracts, vol. 124, No. 23, (Jun. 3, 1996) Abstract No. 316997a.

Igarashi et al., Preparation of 2–azabicyclo[2.2.1] hept–5–en–one, Chemical Abstracts, vol. 121, No. 9 (Aug. 29, 1994) Abstract No. 108525f.

Ono et al., Preparation of 2–azabicyclo[2.2.1] hept–5–en–one, Chemical Abstracts, vol. 121, No. 9 (Aug. 29, 1994) Abstract No. 108526g.

*Primary Examiner*—Johann Richter
*Assistant Examiner*—Jane C. Osweck
*Attorney, Agent, or Firm*—Pillsbury Madison and Sutro LLP

[57] ABSTRACT

The present invention relates to a simplified method of producing ±2-azabicyclo[2.2.1]hept-5-en-3-one from cyclopentadiene and sulfocyanides by reacting cyclopentadiene with sulfonylcyanides without the use of organic solvents.

7 Claims, No Drawings

METHOD OF PRODUCING (+) 2-AZABICYCLO{2.2.1}HEPT-5-EN-3-ONE

BACKGROUND OF THE INVENTION

1. Field of the Invention

The present invention offers a simplified method of producing ±2-azabicyclo[2.2.1]hept-5-en-3-one from cyclopentadiene and sulfocyanides as initial materials in which the target product is obtained in high purity and high yield. ±2-azabicyclo[2.2.1]hept-5-en-3-one is initial material for producing carbocyclic nucleoside analogues which are of interest in medicine on account of their antiviral and chemotherapeutic properties.

2. Prior Art

According to a method described in the literature solid, isolated p-toluene sulfonylcyanide is reacted in a large excess with cyclopentadiene, which functions at the same time as solvent. Vince et al., J. Org. Chem. 43 (1978), 2311; J. C. Jagt et al., J. Org. Chem. 39 (1974), 564. The very unstable intermediate compound 3-tosyl-2-azabicyclo[2.2.1]hepta-2,5-diene, the Diels-Alder product from cyclopentadiene and p-toluene sulfocyanide, is then isolated by concentrating the solution obtained. The solid is subsequently reacted with glacial acetic acid and then hydrolyzed by the addition of water, during which the tosyl group is split off.

In the second method cyclopentadiene and chlorosulfonylisocyanate are added to one another under ring closure and the chlorosulfonyl group split off using sodium sulfite (J. R. Malpass et al., J. Chem. Soc., Perkin I, (1977), 874.

EP-A 0,508,352 teaches a method in which 1,3-cyclopentadiene is reacted with methane sulfonylcyanide in an organic solvent.

EP-A 0,533,048 is relative to a recycling procedure for producing lactams in which the same reaction takes place in the presence of organic solvents and water. The pH of the reaction mixture must be maintained constant during the reaction by the addition of lye. However, as can be read in G. H. Griffiths and F. E. Previdoli (J. Org. Chem. 58 (1993) 6129–6131), the desired product is obtained in aqueous solution with p-toluene sulfinate only in a low yield and in insufficient purity.

A method is described in two Japanese published, unexamined applications (Hei 5-331139 and Hei 5-331140, Dec. 14, 1993) in which the sulfonylcyanides, which are always used as solid substance, are suspended in an organic solvent or water and cyclopentadiene is added to this suspension. A disadvantage of this method is the intermediate isolation of the sulfonylcyanides, which are recognized as not very stable and which can decompose under significant development of heat.

SUMMARY OF THE INVENTION

The invention provides an improved method of producing ±2-azabicyclo[2.2.1]hept-5-en-3-one (RAN). The invention has as subject matter a method of producing 2-azabicyclo[2.2.1]hept-5-en-3-one by reacting 1,3-cyclopentadiene with a substituted sulfonylcyanide in the presence of water and the absence of an organic solvent wherein a) a sulfinate of the general formula $$RSO_2X \qquad (I)$$

in which

R signifies ethyl, propyl, benzyl, 4-methylbenzyl, 4-nitrobenzyl, 2-nitrobenzyl, preferably ethyl, propyl, especially preferably 4-methylbenzyl, benzyl, X signifies an alkali cation Na or K, H is reacted in water as the single solvent with chlorine cyanide to a sulfonylcyanide of the general formula $$RSO_2CN \qquad (II),$$

b) the latter is allowed to react without intermediary isolation subsequently with 1,3-cyclopentadiene, c) the precipitate of the byproduct produced in the reaction (sulfinate) is filtered off, d) the pH of the filtrate is adjusted with an aqueous solution of alkali hydroxide to a value between 7 and 8.5, and e) the desired product is extracted therefrom and obtained by separating off the solvent.

Sulfinates soluble in water are especially suitable. Compounds of this type can be produced in situ, e.g., from the appropriate sulfonyl chlorides and, e.g., sodium sulfite.

The subsequent reaction with chlorine cyanide, which is initiated either in liquid or gas form into the aqueous solution, generally takes place at temperatures of −10° C. to +15° C. The resulting formation of HCl results in a pH of the solution which is in the acidic range. However, the carrying out of the method requires, in contrast to the state of the art, no regulating of this value by the constant addition of, e.g., sodium hydroxide solution. The chlorine cyanide is added in such an amount that it has generally reacted by the addition of the cyclopentadiene.

The developing sulfonylcyanide of the general formula $$RSO_2CN \qquad (II),$$

in which R has the significance cited above, generally accumulates in the form of a solid, so that a suspension forms.

The amount of water is generally approximately 10 to 150 times the molar amount relative to the sulfonylcyanide, especially 20 to 80 times the molar amount. Cyclopentadiene, preferably freshly distilled, is added in a molar ratio of 1 to 2.0 to 1 mole sulfonylcyanide, especially 1 to 1.5, to this suspension, in which the sulfonylcyanide is optionally present in partially dissolved form. The reaction then takes place at a temperature of −10° to +40° C., especially −10° to 30° C.

During this reaction the pH of the reaction mixture is especially between 2.5 and 7. The mixture is agitated until complete reaction, generally 2 to 5 h.

A constant after-regulating of the pH is not necessary.

DETAILED DESCRIPTION OF PREFERRED EMBODIMENTS OF THE INVENTION

The accumulating reaction mixture can be worked up in various ways.

In a preferred embodiment the sulfinic acid accumulating as solid byproduct is separated by suitable filtering steps, the filtrate subsequently brought to a pH of 7 to 8.5, especially approximately 8, and the desired product is obtained after the expelling of an optionally present excess of cyclopentadiene by extraction with an organic, inert solvent.

Organic solvents non-miscible with water such as chlorinated hydrocarbons, ketones, ethers and the like can be considered as extraction agents. Preferred solvents are methylene chloride, methyl tert. butylether, chloroform, methyl isobutylketone., methyl isopropylketone, nitromethane, nitroethane, 1- and 2-nitropropane. The final product is obtained in pure form by concentrating the organic solution by evaporation. The filtration of the p-toluene sulfinic acid accumulation e.g. as byproduct preferably takes place under an atmosphere of nitrogen on account of the decomposition properties. The byproduct is converted by dissolving in C1 to C5 alcohols, preferably methanol, ethanol, n-propanol, isopropanol, into a reliable transport form. Although the byproduct tends to decompose after 30° C. the solutions are stable up to 80° C.

The byproduct can also be suspended in water and dissolved in alkali. The use of sodium hydroxide solution yields, e.g., an aqueous solution of sodium-p-toluene sulfinate. This operational procedure has the advantage that the sulfinate solution can be returned and reacted again to sulfonylcyanide with chlorine cyanide.

Another possibility of not isolating the byproduct precipitate, which is unstable in isolated form, as a solid consists in the neutralizing of the reaction mixture to a pH between 5 and 10, preferably 6.5 and 8.5. This causes the precipitate to go completely into solution. The target product accumulates after the extraction and concentration in pure, crystalline form, in contrast to the state of the art.

The quality of the target product should be further increased by purifying the filtrate separated from the byproduct with activated carbon. The aqueous solution of the target product is generally stabilized beforehand already by pH adjustment to 6.5 to 8.5 and is subsequently optionally purified, extracted and concentrated.

In a preferred variant the sulfonylcyanide is obtained in situ by reacting the corresponding sulfonylchloride with sodium sulfite (JP-OS 5,600,753) and subsequently reacting it with chlorine cyanide.

EXAMPLE 1

60.2 g (0.338 mole) sodium-p-toluene sulfinate were placed in 300 ml water in a receiver, cooled down to −3° C. and 20 ml ClCN added in 10 min. The mixture was agitated 1 h at −3° C. and 37 ml (0.47 mole) freshly produced cyclopentadiene added. The mixture was heated to 18° C. and agitated 3 h at this temperature. The precipitate was then filtered off and dissolved still in the pressure filter with methanol.

The filtrate was brought to pH 8, treated 1 h with activated carbon and extracted with $CH_2Cl_2$. After concentration 29.5 g (0.27 mole) of bright beige RAN were obtained corresponding to 80% yield.

EXAMPLE 2

49 g (0.39 mole) sodium sulfite were dissolved in 350 ml water and the solution heated to 105° C. 68 g (0.357 mole) p-toluene sulfonylchloride were added in several portions in 75 min and the batch agitated 3 h at 100° C. to 105° C. The pH was maintained between 5 and 7 by adding a total of 67 ml 30% NaOH. The reaction mixture was cooled down to −3° C. and then 20 ml chlorine cyanide were added. The mixture was agitated 1 h at this temperature and then 24 g (0.36 mole) cyclopentadiene were added. The reaction mixture was heated to 15° C. and agitated 3 h at this temperature. The precipitated byproduct was filtered off and dissolved in methanol. The filtrate was adjusted to pH 8.6 and the excess cyclopentadiene expelled. The aqueous RAN solution was extracted with methylene chloride and 23.3 g (0.21 mole) bright beige, 97% RAN was obtained after concentration, corresponding to 58% yield.

EXAMPLE 3

60.2 (0.338 mole) sodium-p-toluene sulfinate were placed in 300 ml water in a receiver, cooled down to −3° C. and 20 ml chlorine cyanide added in 10 minutes. The mixture was agitated 1 h at −3° C. and 37 ml (0.47 mole) freshly produced cyclopentadiene added. The mixture was heated to 18° C. and agitated 3 h at this temperature. The mixture was then neutralized with 40 ml 30% NaOH under cooling at 20° to 30° C. The slightly turbid solution was filtered and excess cyclopentadiene expelled and the solution extracted with methylene chloride. After concentration 29.4 g (0.25 mole) 94% yellowish brown RAN were obtained, corresponding to 75% yield.

EXAMPLE 4

49 g (0.39 mole) $Na_2SO_3$ were dissolved in 350 ml water and the solution heated to 100° C. 79.8 g (0.36 mole) nitrobenzosulfonyl chloride were added in several portions and the batch agitated 3 h at 100° C. The pH was maintained between 5 and 7 during the addition of the sulfonylchloride and the post-reaction by adding a total of 60 ml 30% NAOH. After the reaction mixture had been cooled down to −3° C. 20 ml chlorine cyanide were added. The mixture was agitated 1 h at this temperature and then 38 ml (0.5 mole) cyclopentadiene were added. The reaction mixture was heated to 15° C. and agitated 3 h at 15° to 20° C. The precipitated byproduct was filtered off and dissolved in methanol. The filtrate was neutralized and the excess cyclopentadiene expelled. The aqueous solution was extracted with methylene chloride and 21.7 g (0.2 mole) 94% RAN were obtained after concentration, corresponding to 60% yield relative to the sulfinate.

EXAMPLE 5

49 g (0.39 mole) $Na_2SO_3$ and 65.5 g (0.78 mole) $NaHCO_3$ were dissolved in 350 ml water and 46.3 g (0.36 mole) ethane sulfonylchloride slowly added dropwise. The solution was agitated overnight and cooled down to −3° C. before the addition of 19.5 ml (0.39 mole) liquid chlorine cyanide. The mixture was agitated 1 h at 0° C. to −3° C. and the solution subsequently compounded with 38 ml (0.48 mole) cyclopentadiene. After being heated to 15° C. the mixture was agitated 3 h. The slightly turbid solution was filtered with 20 ml 30% NaOH and excess cyclopentadiene was expelled. After extraction and concentration 19.5 g 95% (0.17 mole) RAN was obtained, corresponding to 59% yield relative to the sulfinate.

EXAMPLE 6

1,600 g (8.664 moles) sodium-p-toluene sulfinate were placed in 7 l water in a receiver, cooled down to −3° C. and 475 ml (9.44) [sic-moles?] chlorine cyanide added in 10 minutes. The mixture was agitated 1 h at −3° C. and 750 g (11.35 moles) cyclopentadiene added. The mixture was heated to 18° C. and agitated 3 h at this temperature. The precipitate (1,327 g) was then filtered off and the filtrate brought to pH 8.5.

The workup was performed in analogy with example 1. 715.7 g RAN were obtained, corresponding to 75.5% yield.

144 g of the filtered-off precipitate were suspended in 500 ml water. The pH was brought to 12.7 by adding 64 g 50% sodium hydroxide solution and the suspension agitated 1 h. After filtration 629 g of a 19% sodium-p-toluene sulfinate solution (0.671 mole) were obtained. The solution was cooled down to −3° C. and 40 ml chlorine cyanide (0.795 mole) added. After 1 h agitation at −3° C. 63 g (0.953 mole) cyclopentadiene were added. The mixture was then agitated 3 h at 20° C. The solution was filtered, brought to pH 8.6 and worked up analogously to example 1. 29 g 93.7% RAN were obtained, corresponding to 37.1% yield.

What is claimed is:

1. A method of producing a 2-azabicyclo{2.2.1}hept-5-en-3-one product by reacting 1,3-cyclopentadiene with a substituted sulfonylcyanide in the presence of water, comprising:

a) reacting a sulfinate of the general formula $$RSO_2X \qquad (I)$$

in which R signifies ethyl, propyl, benzyl, 4-methylbenzyl, 4-nitrobenzyl, or 2-nitrobenzyl, X signifies an alkali cation Na or K, or H, in water as a single solvent with chlorine cyanide to produce a sulfonylcyanide of general formula $$RSO_2CN \qquad (II),$$

b) subsequently reacting the sulfonylcyanide without intermediary isolation, with 1,3-cyclopentadiene,
c) filtering off a sulfinate precipitate of a byproduct, produced in the reaction, to produce a filtrate,
d) adjusting pH of the filtrate with an aqueous solution of alkali hydroxide to a pH value between 7 and 8.5, and
e) isolating the product from the filtrate by extraction.

2. The method according to claim 1, wherein the filtrate is purified with activated carbon.

3. The method according to claim 1, wherein the filtered sulfinate is dissolved in a $C_1$–$C_5$ alcohol.

4. The method according to claim 1, wherein the filtered sulfinate is dissolved in aqueous alkali-hydroxide- or -carbonate solution.

5. The method according to claim 4, wherein the obtained solutions of the sulfinate are used as initial compounds for the method.

6. The method according to claim 1, wherein the sulfonylcyanide is produced in situ by reacting the corresponding sulfonylchloride with sodium sulfite.

7. The method according to claim 1, wherein cyclopentadiene and sulfonylcyanide are used in a ratio of 1 up to 1.5 to 1.

* * * * *